US011748616B2

(12) United States Patent
Ravuna et al.

(10) Patent No.: US 11,748,616 B2
(45) Date of Patent: Sep. 5, 2023

(54) DETECTION OF ACTIVATION IN ELECTROGRAMS USING NEURAL-NETWORK-TRAINED PREPROCESSING OF INTRACARDIAC ELECTROGRAMS

(71) Applicant: BIOSENSE WEBSTER (ISRAEL) LTD., Yokneam (IL)

(72) Inventors: Eliyahu Ravuna, Kiryat Ata (IL); Natan Sharon Katz, Atlit (IL); Andrey Evgenyevich Kiryasov, Chelyabinsk (RU); Elena Igorevna Kuzhnareva, Moskovskaya obl (RU); Aleksey Vladimirovich Shovkun, Moscow (RU)

(73) Assignee: Biosense Webster (Israel) Ltd., Yokeam (IL)

( * ) Notice: Subject to any disclaimer, the term of this patent is extended or adjusted under 35 U.S.C. 154(b) by 367 days.

(21) Appl. No.: 16/991,766

(22) Filed: Aug. 12, 2020

(65) Prior Publication Data

US 2022/0051091 A1 Feb. 17, 2022

(51) Int. Cl.
*G06N 3/08* (2023.01)
*A61B 5/349* (2021.01)
(Continued)

(52) U.S. Cl.
CPC .............. *G06N 3/08* (2013.01); *A61B 5/287* (2021.01); *A61B 5/339* (2021.01); *A61B 5/349* (2021.01); *A61B 5/7267* (2013.01); *G06N 3/04* (2013.01)

(58) Field of Classification Search
CPC . G06N 3/08; G06N 3/04; A61B 5/287; A61B 5/339; A61B 5/349; A61B 5/7267;
(Continued)

(56) References Cited

U.S. PATENT DOCUMENTS 5,092,343 A 3/1992 Spitzer
5,251,626 A 10/1993 Nickolls
(Continued)

FOREIGN PATENT DOCUMENTS

CA 2942904 A1 10/2015
CN 104523264 A 4/2015
(Continued)

OTHER PUBLICATIONS

European Search report for corresponding EPA No. 21190821.5 dated Jan. 4, 2022.

*Primary Examiner* — Michael A Keller (57) ABSTRACT

A method includes collecting a plurality of bipolar electrograms and respective unipolar electrograms of patients, the electrograms including annotations in which one or more human reviewers have identified and marked a window-of-interest and one or more activation times inside the window-of-interest. A ground truth data set is generated from the electrograms, for training at least one electrogram-preprocessing step of a Machine Learning (ML) algorithm. The ML algorithm is applied to the electrograms, to at least train the at least one electrogram-preprocessing step, so as to detect an occurrence of an activation in a given bipolar electrogram within the window-of-interest.

16 Claims, 6 Drawing Sheets

(51) Int. Cl.
*A61B 5/339* (2021.01)
*A61B 5/287* (2021.01)
*A61B 5/00* (2006.01)
*G06N 3/04* (2023.01)

(58) Field of Classification Search
CPC ......... A61B 5/283; A61B 5/318; A61B 5/346; A61B 5/72; A61B 5/7264; G16H 50/20
See application file for complete search history.

(56) References Cited

U.S. PATENT DOCUMENTS

| | | | |
|---|---|---|---|
| 8,260,407 B1 * | 9/2012 | Rhude | A61B 5/0031 600/509 |
| 2004/0059237 A1 | 3/2004 | Narayan | |
| 2015/0208938 A1 | 7/2015 | Houben | |
| 2018/0042504 A1 * | 2/2018 | Botzer | A61B 5/7239 |
| 2019/0354568 A1 * | 11/2019 | Lindberg | H03H 17/028 |

FOREIGN PATENT DOCUMENTS

| | | | | |
|---|---|---|---|---|
| CN | 110353665 A | 10/2019 | | |
| KR | 2020071183 A | 6/2020 | | |
| WO | WO-2018195052 A1 * | 10/2018 | ............. | A61B 34/20 |
| WO | WO2020226534 A1 | 11/2020 | | |

* cited by examiner

DETECTION OF ACTIVATION IN ELECTROGRAMS USING NEURAL-NETWORK-TRAINED PREPROCESSING OF INTRACARDIAC ELECTROGRAMS

FIELD OF THE INVENTION

This invention relates generally to analysis of intracardiac electrophysiological signals, and specifically to evaluation of electrical propagation in the heart using machine leaning (ML).

BACKGROUND OF THE INVENTION

In a patient suffering from cardiac arrhythmia, impulses of the electrical activity may follow a pathologic path in cardiac tissue. In an electrophysiological study, one of the goals of the physician is to understand the paths followed by the impulse of the electrical activity, e.g., by inserting a multi-electrode catheter into the heart of the patient and measuring intracardiac ECG signals via the catheter. Typically, the catheter is threaded through blood vessels to the heart to measure the electrical activity in the endocardium. Alternatively, the catheter may be inserted from an incision in the chest in order to measure the electrical activity in the epicardium.

To measure the electrical activity, some electrodes of the catheter are brought into contact with the heart tissue (either endocardium or epicardium) to acquire electrical potential difference between the electrodes and a ground, such as the Wilson Central Terminal ground. An electrical potential difference between a catheter electrode and the ground is called the unipolar signal of the electrode. An electrical potential difference between two adjacent electrodes of the catheter is called the bipolar signal between the electrodes.

During an electrophysiology study, in order to understand the paths followed by the impulse of the electrical activity, the physician needs to know the time at which the impulse passed under each one of the electrodes. However, by looking to the electric potential difference between a bipolar pair, one cannot know when the impulse of the electrical activity passed under each electrode.

This problem can be overcome by analyzing bipolar and unipolar signals simultaneously, as described U.S. Patent Application Publication No. 2018/0042504, as further described below. However, interpreting unipolar signals is challenging, especially because of the noise on unipolar signals. For example, unlike bipolar signals, unipolar signals may contain an excessive amount of far-field noise. This is what makes the analysis of unipolar signals challenging.

As noted above, computer aided analysis of intracardiac signals using both bipolar and unipolar signals, in order to determine the timing of the cardiac activation, was previously suggested in U.S. Patent Application Publication No. 2018/0042504. This patent application describes a rule-based algorithm and method, including receiving a bipolar signal from a pair of electrodes in proximity to a myocardium of a human subject and receiving a unipolar signal from a selected one of the pair of electrodes. The method further includes computing a local unipolar minimum derivative of the unipolar signal, and a time of occurrence of the unipolar minimum derivative. The method also includes computing a bipolar derivative of the bipolar signal, evaluating a ratio of the bipolar derivative to the local unipolar minimum derivative, and when the ratio is greater than a preset threshold ratio value, identifying the time of occurrence as a time of activation of the myocardium.

SUMMARY OF THE INVENTION

An embodiment of the present invention that is described hereinafter provides a method including collecting a plurality of bipolar electrograms and respective unipolar electrograms of patients, the electrograms including annotations in which one or more human reviewers have identified and marked a window-of-interest and one or more activation times inside the window-of-interest. A ground truth data set is generated from the electrograms, for training at least one electrogram-preprocessing step of a Machine Learning (ML) algorithm. The ML algorithm is applied to the electrograms, to at least train the at least one electrogram-preprocessing step, so as to detect an occurrence of an activation in a given bipolar electrogram within the window-of-interest.

In some embodiments, each bipolar electrogram is acquired from a pair of electrodes placed at a location in a heart of a patient, and a respective unipolar electrogram is acquired from one electrode of the pair of electrodes.

In some embodiments, collecting the bipolar electrograms and the respective unipolar electrograms includes collecting multiple bipolar electrograms and respective unipolar electrograms from multiple electrode pairs of a multi-electrode catheter.

In an embodiment, the at least one electrogram-preprocessing step includes performing one or more convolutions of the electrograms with a set of convolutional kernels, and wherein training the at least one electrogram-preprocessing step includes specifying coefficients of the convolutional kernels.

In another embodiment, the at least one preprocessing step of the electrograms includes point-by-point multiplication between a bipolar electrogram filtered by one of the convolutional kernels and a respective unipolar electrogram filtered by another one of the convolutional kernels, and wherein applying the ML algorithm includes inputting a multiplication signal resulting from the point-by-point multiplication to the ML algorithm.

In some embodiments, the method further includes presenting the given bipolar electrogram to a user, with an annotation thereon marking a time of detected activation.

In some embodiments, applying the ML algorithm includes applying an artificial neural network (ANN).

In some embodiments, the method further includes receiving for inference a bipolar electrogram and a respective unipolar electrogram of a patient, and a window-of-interest. Using the trained ML algorithm, the occurrence of an activation in the bipolar electrogram is detected and the activation is associated with the heart tissue location in contact with the electrode acquiring the respective unipolar electrogram.

There is additionally provided, in accordance with another embodiment of the present invention, a system including one or more displays and one or more processors. The one or more displays are configured to present annotated electrograms. The one or more processors are configured to (a) collect a plurality of bipolar electrograms and respective unipolar electrograms of patients, the electrograms including annotations in which one or more human reviewers have, using the one or more processors and the respective one or more displays, identified and marked a window-of-interest and one or more activation times inside the window-of-interest, (b) generate, from the electrograms, in at least one of the one or more processors, a ground truth data set for training at least one electrogram-preprocessing step of a Machine Learning (ML) algorithm, and (c) apply the ML algorithm to the electrograms, to at least train the at least one electrogram-preprocessing step, so as to detect an occurrence of an activation in a given bipolar electrogram within the window-of-interest.

There is further provided, in accordance with another embodiment of the present invention, a method for identifying activations in cardiac electrograms using a Machine Learning (ML) model having at least one electrogram-preprocessing step, the method including training the at least one electrogram-preprocessing step of the ML model. Using the ML model, within a window-of-interest, an activation is identified in a bipolar electrogram using a respective unipolar electrogram.

In some embodiments, training the at least one electrogram-preprocessing step includes optimizing coefficients of convolutional kernels being convolved with the electrograms during preprocessing.

In some embodiments, identifying the activation includes generating, by the ML model, a respective probability for each of multiple possible activation values in the window of interest.

In an embodiment, identifying the activation includes selecting one of (i) an activation with the highest probability, (ii) one or more activations with a probability above a given threshold, and (iii) one or more activations with a probability above a variable threshold.

There is furthermore provided, in accordance with another embodiment of the present invention, a computer software product, the product including a tangible non-transitory computer-readable medium in which program instructions are stored, which instructions, when read by a processor, cause the processor to:

apply a Machine Learning (ML) algorithm comprising at least one trainable electrogram-preprocessing step, to a ground truth data set of annotated electrograms for training the at least one electrogram-preprocessing step of the ML algorithm so as to detect an occurrence of an activation in a given bipolar electrogram within a window-of-interest, wherein the ground truth data set of annotated electrograms is generated by collecting a plurality of bipolar electrograms and respective unipolar electrograms of patients, the electrograms including annotations in which one or more human reviewers have identified and marked the window-of-interest and one or more activation times inside the window-of-interest.

BRIEF DESCRIPTION OF THE DRAWINGS

The present disclosure will be more fully understood from the following detailed description of the embodiments thereof, taken together with the drawings, in which.

DETAILED DESCRIPTION OF EMBODIMENTS

Overview

Intracardiac electrophysiological (EP) mapping is a catheter-based method that is sometimes applied to characterize cardiac EP wave propagation abnormalities, such as those that cause an arrhythmia. In a typical catheter-based procedure, a distal end of a catheter, which comprises multiple sensing electrodes, is inserted into the heart to collect a set of data points comprising (i) measured locations on a wall tissue of a cardiac chamber and (ii) respective EP signals, from which the EP mapping system can produce an EP map. An example of an EP map that is useful in diagnosing arrhythmia is an EP timing diagram map, called a local activation time (LAT) map, of regions of the cardiac chamber wall tissue.

To generate an LAT map, a processor may have to analyze intracardiac ECG signals collected at various points in the heart, called hereinafter electrograms (EGM), to identify an activation in each signal (i.e., in a waveform of an EGM), and to annotate the activation and calculate an LAT value.

An annotation time represents the time where the cardiac impulse passed at a specific cardiac tissue location, as measured by the catheter. Since different EGM signals are collected at different times, a gated measurement technique is required to align the signals collected at different times. In the domain of cardiac electrophysiology, the "gate" used for the gated measurement is called the reference annotation. For example, the R peak of the QRS signal of the body surface ECG, or an activation detected inside the coronary sinus, activations detected at the high-right-atrium or a more sophisticated method fed by multiple signals may be used as the reference annotation. The LAT value is defined as the difference between the mapping annotation time and the reference annotation time.

Some embodiments of the present invention that are described hereafter provide a machine learning (ML) technique and algorithm configured to train both a preprocessing module and an artificial neural network (ANN) model of the algorithm. After pairs of a bipolar signal and a respective unipolar EGM signal are preprocessed by a trained preprocessing module, a processor analyzes the preprocessed signals, to determine the exact timing of the activation under each one of the catheter electrodes.

In preparation for training, a plurality of electrograms are collected from multiple sites (e.g., hospitals), the electrograms comprising annotations in which one or more human reviewers have, using the one or more processors, identified and marked activation times. Typically the annotation of activations were verified and/or corrected by numerous experts who are skilled at analyzing diagnostic cardiac electrograms.

One or more skilled persons (e.g., a clinical application engineer, or an algorithm engineer) compile, from the collection of annotated electrograms, a ground truth data set to be used for the training of the provided ML algorithm.

During training and inference, the two components of the algorithm (i.e., preprocessing and ANN) work together to identify activations in electrogram input. To this end a processor applies the ML algorithm to the electrograms, to at least train at least one electrogram-preprocessing step, so as to detect an occurrence of an activation in a given bipolar electrogram.

In some embodiments, either during training or inference, the disclosed model looks for an activation that is present in both bipolar and respective unipolar EGM signals. Using the unipolar EGM, the model determines a time of activation on the bipolar EGM, and the tissue location of the activation (e.g., under the electrode from which the unipolar EGM was acquired). When applied to the numerous electrograms, the disclosed algorithm can generate a reliable database for generating an electrophysiologically accurate LAT map of at least a portion of a cardiac chamber.

To well-define the algorithm, the ML model (e.g., the ANN model) is applied to the unipolar and bipolar signals via a sliding window. The output of the ANN model is a probability associated with a LAT value, or a set of probabilities associated with every possible LAT value in the window-of-interest.

The training is typically performed using a loss function, such as a cross-entropy function, where, for example, when the calculated LAT value is equal to a ground truth LAT value, the loss is defined as zero (0). The loss function arguments may comprise a set of differences between the algorithm-estimated LAT value and a respective verified LAT value (ground truth). The LAT difference is well defined only within a window of interest (WOI), such as having an effective width of cardiac cycle-length. Arguments outside the WOI are ignored.

The loss function is defined such that a zero LAT difference contributes zero loss to the total loss, whereas when the difference between calculated and expected LAT values is above a predefined value, such as 5 milliseconds, the contributed loss asymptotically approaches to a maximum value (e.g., a normalized value of one). For EP signals analyzed in this application, a 5 milliseconds width of a loss function (e.g., at loss=½) was found to be adequate to make the ML algorithm converge sufficiently fast in the presence of noise with sufficient estimation precision (e.g., of ±1 mSec).

Typically, during training, the disclosed technique optimizes the preprocessing module of the algorithm, so that the preprocessing module includes correct high-pass, low-pass, band-pass and/or band-stop convolutional filters (i.e., kernels) to flatten and smoothen the EGM signals, and to emphasize the required features of EGM signals, and thus to be able to accurately determine a presence of activation-indicative features that are present on both bipolar and unipolar signals simultaneously.

Searching for such activation-indicative features that are present, at the same time, in both bipolar and unipolar EGMs, is roughly equivalent to searching for such a pattern in the multiplication of the signals. Thus, in an embodiment, the preprocessing module multiplies bipolar and unipolar EGMs that were acquired at the same location point-by-point with one another. The resulting multiplication signals are concatenated with the signals themselves and input to the ANN. The advantage of using multiplication signals in an input layer of an ANN, in addition to using the signals themselves, lies in improving the capabilities of the ANN model to detect the activation-indicative amplitude, as multiplication emphasizes the temporal coincidence of such an amplitude in the bipolar signals of the respective unipolar signals.

The convolution filter is optimized by training, for example, to overcome low-frequency wandering baseline artifacts and high-frequency noise artifacts. First, the algorithm learns a sufficiently optimal convolution filter (via training the neural network with numerous signals). In the very first iteration of the training, the convolutional kernels are typically made of random numbers, or other numbers, such as "all ones" or "all zeros." Regardless, the training iterations optimize the kernel numbers and the ANN module as a whole.

Once the algorithm applies a sufficiently optimized convolution filter for both the bipolar signal and its respective unipolar signal, the multiplication of the convolutions has an increased effect on the training to further optimize preprocessing and ANN parameters.

In some embodiments, multiple convolution filters may be applied in parallel to a same signal. Every convolution filter may be trained to extract a different feature of bipolar or unipolar signals.

The training produces optimized parameters of the preprocessing module, such as a kernel parameter vector $\{\vec{x}\}$, and optimized parameters of the ANN, such as a weights and biases vector $\{\vec{w}\}$. The optimized parameters may be transferred to a user who applies the technique, having the algorithm preinstalled on the user site, for instance, using a secured memory stick or via the Internet.

Numerous types of ML models are available for use, and, besides the ANN model used here as an example, a person skilled in the art may choose a different ML model, including decision tree learning, support vector machines (SVM) and Bayesian networks. ANN models include, for example, convolutional NN (CNN), recursive NN (RNN), Long Short-Term Memory (LSTM), enforcement learning, autoencoder, and probabilistic neural network (PNN). Typically, the one or more processors used (collectively named hereinafter "processor") are programmed in software containing a particular algorithm that enables the processor to conduct each of the processor-related steps and functions outlined above. Typically, the training is done using a computing system comprising multiple processors, such as graphics processing units (GPU) or tensor processing units (TPU). However, any of these processors may be also be central processing units (CPU).

In some embodiments, the disclosed technique detects single activations (i.e., finds one LAT value per input electrogram waveform). In other embodiments, the technique is used to detect fractionated ECG signals, local abnormal ventricular activity (LAVA) indicative signals, late potentials, double potentials and split potentials. An embodiment designed to detect regular activations may choose the LAT value with the highest probability. An embodiment designed to detect double, split, fractionated, fragmented or any kind of multiple potentials may choose all LAT values with a probability above a given constant threshold. An embodiment designed to detect late potentials can use a variable threshold (e.g., descending), in a way that the later the LAT, the higher the threshold is. An embodiment to detect early potential can do the opposite.

After training with 800,000 atrial ECG signals, the inventors have achieved a 95 percent success rate in analyzing 3.1 million electrograms (i.e., by performing inference with the trained algorithm) that did not participate in the training.

The disclosed ANN-based EP signal analysis technique may improve the value of diagnostic catheterization procedures by providing a physician reliable diagnostics.

System Description

Figure 1:
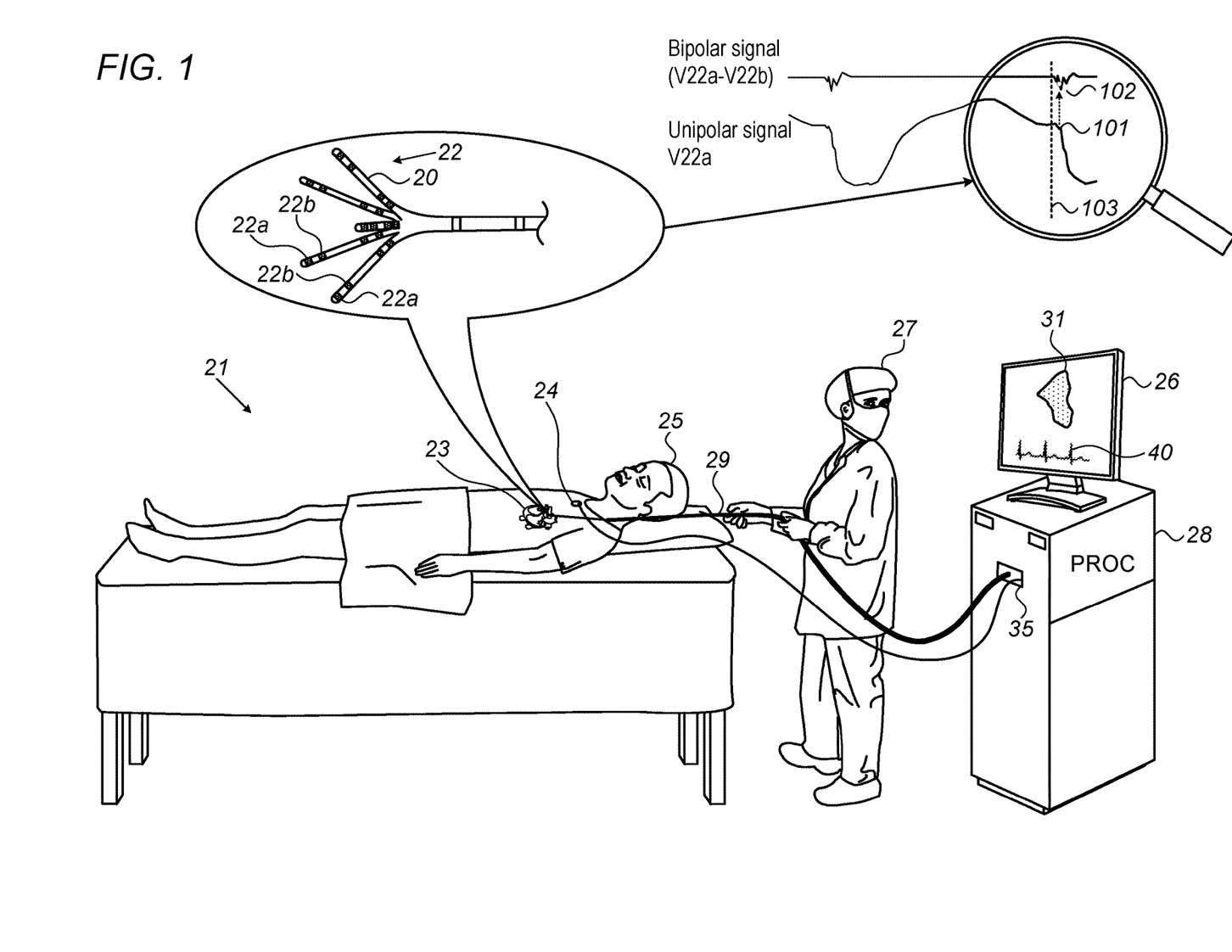
FIG. 1 is a schematic, pictorial illustration of a catheter-based electrophysiological (EP) mapping system, which is configured to detect an activation time in an electrogram (EGM), in accordance with an exemplary embodiment of the present invention.

FIG. 1 is a schematic, pictorial illustration of a catheter-based electrophysiological (EP) mapping system 21, which is configured to detect an activation time in an electrogram (EGM), in accordance with an exemplary embodiment of the present invention. FIG. 1 depicts a physician 27 using EP mapping catheter 29 to perform EP mapping of a heart 23 of a patient 25. Mapping catheter 29 comprises, at its distal end, one or more arms 20, each of which is coupled to a bipolar electrode 22 comprising adjacent electrodes 22a and 22b. A bipolar signal acquired by catheter 29 is defined herein as a potential difference between adjacent electrodes 22a and 22b.

To acquire unipolar signals from electrodes 22a and/or 22b, a Wilson central terminal (WCT) ground is formed from three body surface electrodes 24 (attached to the skin of a patient). For example, three body surface electrodes 24 may be coupled to the patient's chest. (For ease of illustration, only one external electrode 24 is shown in FIG. 1.)

A bipolar signal is easier to interpret, but it is less precise. A respective unipolar signal is more precise, but it is more prone to far-field noise. If a user looks to the bipolar signal only, he/she cannot differentiate an activation on the first or second electrode. If a user looks to the unipolar signal only, the user can get numerous false detections. To find the most precise activation times, the disclosed technique applies an ML algorithm to searches for the features predicting electrical activation in the pairs of unipolar and bipolar signals simultaneously, as described below.

During the mapping procedure, the locations of electrodes 22 are tracked while they are inside heart 23 of the patient. For that purpose, electrical signals are passed between electrodes 22 and body surface electrodes 24 (typically, three additional body surface electrodes may be coupled to the patient's back). Based on the signals, and given the known positions of electrodes 24 on the patient's body, a processor 28 calculates an estimated location of each electrode 22 within the patient's heart. Such tracking may be performed using the Active Current Location (ACL) system, made by Biosense-Webster (Irvine Calif.), which is described in U.S. Pat. No. 8,456,182, whose disclosure is incorporated herein by reference.

The processor associates a signal acquired by electrodes 22, such as unipolar or bipolar EGMs, with the location at which the signal was acquired. Processor 28 receives the signals via an electrical interface 35, and uses information contained in these signals to construct an EP map 31 and EGMs 40, and to present them on a display 26.

Figure 3:
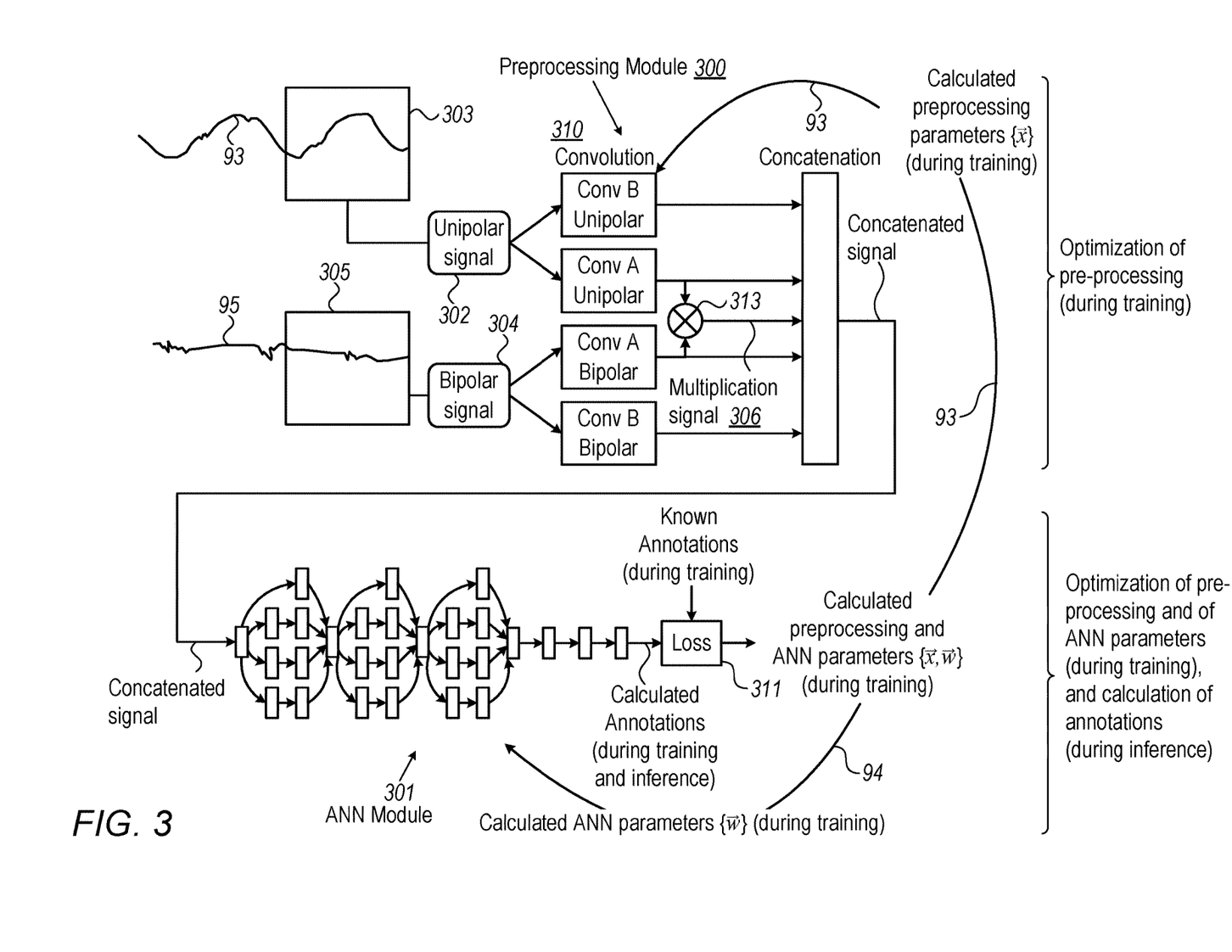
FIG. 3 is a block diagram that schematically describes an algorithm for the detection of activation times in electrograms (EGM), according to an exemplary embodiment of the present invention.

In the illustrated embodiment, using algorithms comprising an ML algorithm, such as disclosed in FIG. 3, processor 28 calculates local activation time (LAT) values to generate an LAT map. The ML algorithm is trained to find an LAT value at a specific tissue location.

The training, as described in FIG. 3, is largely based on the following approach, that a human expert reviewer would have likely executed: Look into the bipolar EGM signal (V22a-V22b), and, from that location, understand the approximate timing of the cardiac wavefront activation, and then search for an activation pattern in a respective unipolar EGM, V22a, to find the exact timing of the cardiac wavefront activation. As can be seen under the magnifying glass callout, an identified irregularity 101 in the unipolar signal (although a very tiny feature) is at the exact location of the activation time (102), and an LAT value is calculated with a time difference between time 102 and a baseline time 103. As the training steps iterate, the aforementioned ML algorithm is expected to imitate the decisions of the human expert reviewer by:

shaping the preprocessing parameters of the bipolar signal in a way that the parameters will emphasize the features of the activations seen on bipolar EGMs, shaping the preprocessing parameters of the unipolar signals in a way to remove the wandering baseline and to emphasize the features of the activations seen on unipolar EGMs, shaping the machine learning parameters to interpret these features to calculate the probability of the activation per each LAT value in the window of interest.

The illustrated signals are a simplified example, to illustrate the concepts only. In real-life, signals can be noisier than this illustration.

Processor 28 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 28 runs a dedicated algorithm as disclosed herein, including in FIGS. 3, 4, and 5, that enables processor 28 to perform the disclosed steps, as further described below. In some cases, processor 28 includes enhanced computation capacities, for example, by using the aforementioned GPUs or TPUs.

The example illustration shown in FIG. 1 is chosen purely for the sake of conceptual clarity. Other types of electrophysiological sensing catheter geometries, such as the Lasso® Catheter (produced by Biosense-Webster Inc., Irvine, Calif.) may be employed. Additionally, contact sensors may be fitted at the distal end of mapping catheter 29 and transmit data indicative of the physical quality of electrode contact with tissue. In an embodiment, measurements of one or more electrodes 22 may be discarded if their physical contact quality is indicated as poor, and the measurements of other electrodes may be regarded as valid if their contact quality is indicated as sufficient.

Training and Deployment of the Trained ML Model

Figure 2:
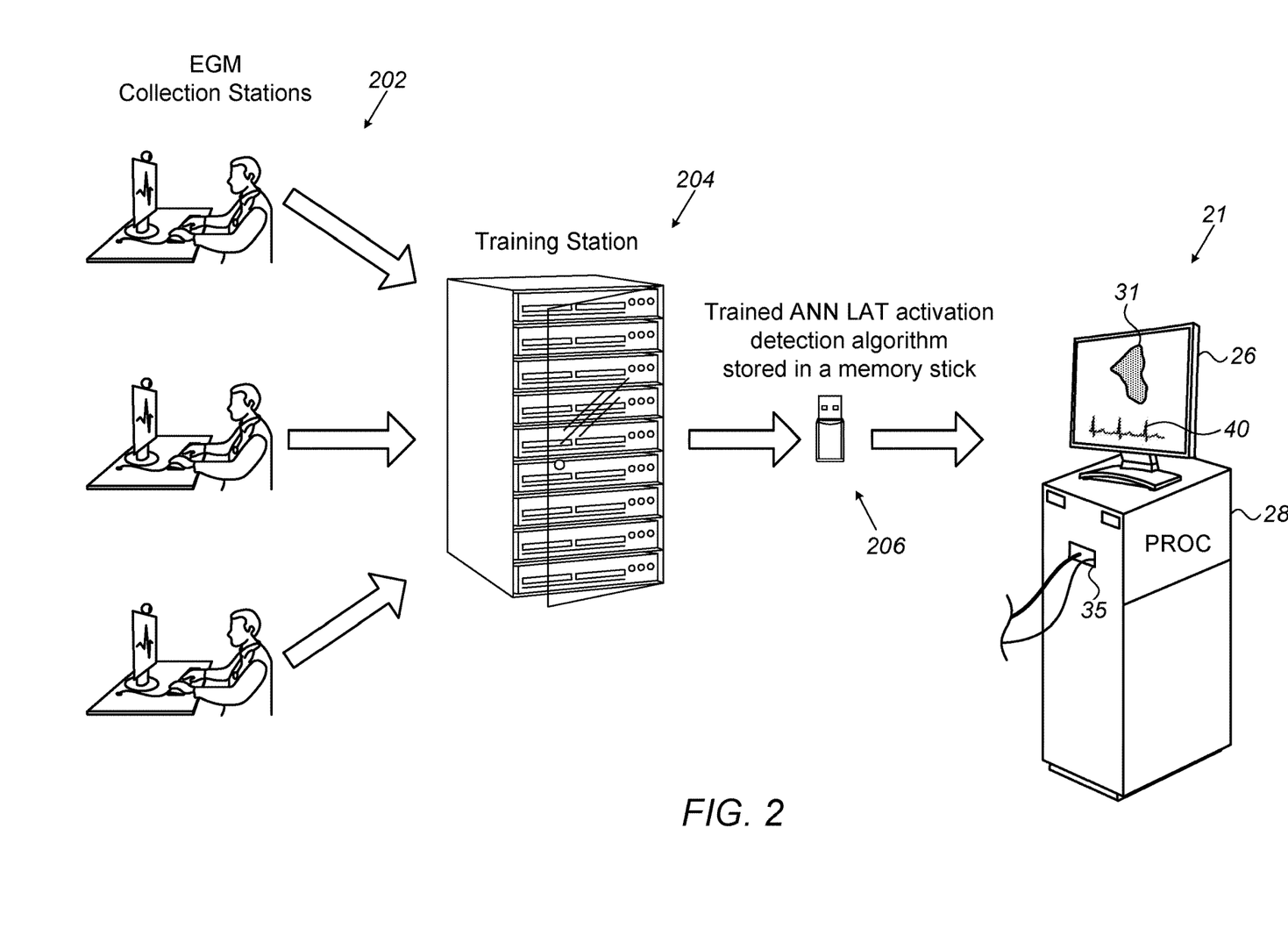
FIG. 2 is a schematic illustration of a workflow describing training and deployment of an algorithm for the detection of an activation time in an electrogram (EGM), according to an exemplary embodiment of the present invention.

FIG. 2 is a schematic illustration of a workflow describing training and deployment of an algorithm (e.g., one comprising an ANN and a trainable preprocessing model) for the detection of an activation time in an electrogram (EGM), according to an embodiment of the present invention. As seen, collection of a training set of EGMs is done at numerous sites 202, where, at each site, a physician collects numerous correlated bipolar and unipolar EGMs that the physician verifies as correctly annotated with activation times (e.g., such as the annotation 102 of FIG. 1). The physician may manually correct wrong annotations of activations. This verified set of annotations is used during an ANN training session at a training station 204 in order to fine-tune annotations performed by the ANN during training by minimizing a loss function of the ANN, so as to generate a set of ANN parameters $\{\vec{w}\}$, and preprocessing parameters $\{\vec{x}\}$, for use in inference of new EGMs as described by FIG. 3.

The resulting trained ANN LAT activation detection algorithm can be stored (206) in a memory stick, and provided to users of system 21 of FIG. 1, or to users of other relevant diagnostic systems.

The example illustration shown in FIG. 2 is chosen purely for the sake of conceptual clarity. For example, the trained model may be sent via the web rather than using a memory stick. The training may be performed using distributed computation, rather than a training station.

Neural-Network-Trained Preprocessing of Electrograms

FIG. 3 is a block diagram that schematically describes an algorithm for the detection of activation times in electrograms (EGM), according to an embodiment of the present invention.

As seen, the disclosed deep learning model is divided into two parts, a preprocessing module 300 and an ANN module 301. Preprocessing module 300 includes a set of convolution kernels (310) having parameters $\{\vec{x}\}$ to be optimized. ANN module 301 has a set of weights and biases $\{\vec{w}\}$ to be optimized.

The raw EGM input to the model comprise correlated portions of raw unipolar and bipolar signals (93, 95), where the portions are selected one after the other by applying sliding windows 303 and 305, respectively.

During training, intermediately optimized parameters $\{\vec{x}\}$ and $\{\vec{w}\}$ are backpropagated (93, 94) to the different modules in order to optimize modules 300 and 301, respectively. The training process is iterative and ends when a given end criterion is achieved, thereby delivering, in this way, a final set of optimized parameters $\{\vec{x}, \vec{w}\}$. The end criterion may be the convergence of the sum of the loss, the convergence of the parameters, the achievement of a loss value lower than some threshold, a timeout or a combination of them.

In the illustrated embodiment, to optimize parameters $\{\vec{x}, \vec{w}\}$, a loss function 311 of ANN module 301 minimizes a difference loss between a known annotation of an EGM and the ANN calculated annotation.

As noted above, a central feature of the disclosed technique (e.g., algorithm) is the training of the preprocessing step, e.g., by optimizing convolution kernels applied to time-windowed (303, 305) EGM signals (93, 95), namely, to unipolar signal 302 (e.g., V22a of FIG. 1) and bipolar signal 304 (e.g., V22a-V22b of FIG. 1).

Preprocessing module 300 may include any number of convolution kernels, with a typical number being between four and eight, so as to increase the flexibility of training to find optimize kernels. Each convolution kernel may "learn" to emphasize a different feature of the signal. The preprocessing phase and the ML algorithm are optimized, by the iterations of the trainings, to identify which features need to be emphasized. For example, although it is reasonable to assume that the convolution kernels associated with unipolar signals will learn to remove the wandering baseline, this is not something defined by the designer of the algorithm, this should occur as a natural result of the training.

In general, a convolution filter acts as a finite impulse response (FIR) filter. The convolution may act as a low-pass, high-pass, band-stop or band-pass filter type.

As noted above, numerous kernels may be included in a search of optimized parameters $\{\vec{x}\}$, such as the types and sharpness of the optimized kernels.

An important feature of preprocessing module 300 is inputting multiplication signals. As seen, the convolved unipolar and bipolar signals are multiplied (313) point by point, and the multiplication signal 306 is input with the other convolved signals. As noted above, any number of convolution kernels "A" may be used, and a same number of different resulting multiplication signals are input, in a form of a concatenated input vector, to ANN module 301.

The motivation for using multiplication signals is to utilize, for training modules 300 and 301, the temporal correlation between the unipolar and bipolar signals, as exemplified in FIG. 1 with signals V22a-V22b and V22a.

During inference, the same deep learning model is used to analyze new EGM signals, with the deep learning model parameters comprising the optimized parameters $\{\vec{x}, \vec{w}\}$. During the inference, the ML model (e.g., a CNN comprising a RESNET network) provides the activation time at which to annotate the bipolar signal, in order to subsequently extract an LAT value.

Some embodiments of the disclosed invention receive as input a fixed number of signal samples (e.g., receive a digitized signal of a given duration), however the physician is typically interested in a specific window-of-interest, which depends on the cycle length of patient's current arrhythmia. To overcome this problem, both in the training and the inference phase, probabilities of LAT values outside the window of interest are zeroed out just before normalizing the distribution, for example using the SoftMax function.

Zeroing all probability values outside the window of interest ensures that the sum of the probabilities is still one after the normalization step and that the window-of-interest is correctly taken in consideration in both training and inference phases.

The following pseudocode example is of the convolution preprocessing and signal multiplication steps with k convolutions for unipolar signals, k convolutions for the bipolar signals, where p≤k of each of the bipolar and respective unipolar signals are point-by-point multiplied to generate p multiplication signals. In this notation, $\{\vec{x}\}$ values are the parameters of the different kernels.

```
function Preprocessing(unipolarSignal, bipolarSignal, {x⃗}) →
preprocessed signals
begin
   u₁ = convolution(unipolarSignal, x₁)
   u₂ = convolution(unipolarSignal, x₂)
   .
   uₖ= convolution(unipolarSignal, xₖ)
   bₖ₊₁ = convolution(bipolarSignal, xₖ₊₁)
   bₖ₊₂ = convolution(bipolarSignal, xₖ₊₂)
   .
   Bₘ = convolution(bipolarSignal, xₘ)
   m₁ = PointByPointMultiplication(u₁, b₁)
   m₂ = PointByPointMultiplication(u₂, b₂)
   .
   mₚ= PointByPointMultiplication(uₚ, bₚ)
   return {u₁, u₂,... uₖ, bₖ₊₁, bₖ₊₂, ...bₘ, m₁, m₂, ...mₚ}
end
```

The example block diagram shown in FIG. 3 is chosen purely for the sake of conceptual clarity. ANN module 301 is a schematic module, shown only conceptually, where ANN module 301 represents selection from numerous possible ANN embodiments, including a library-coded ANN function.

Figure 4:
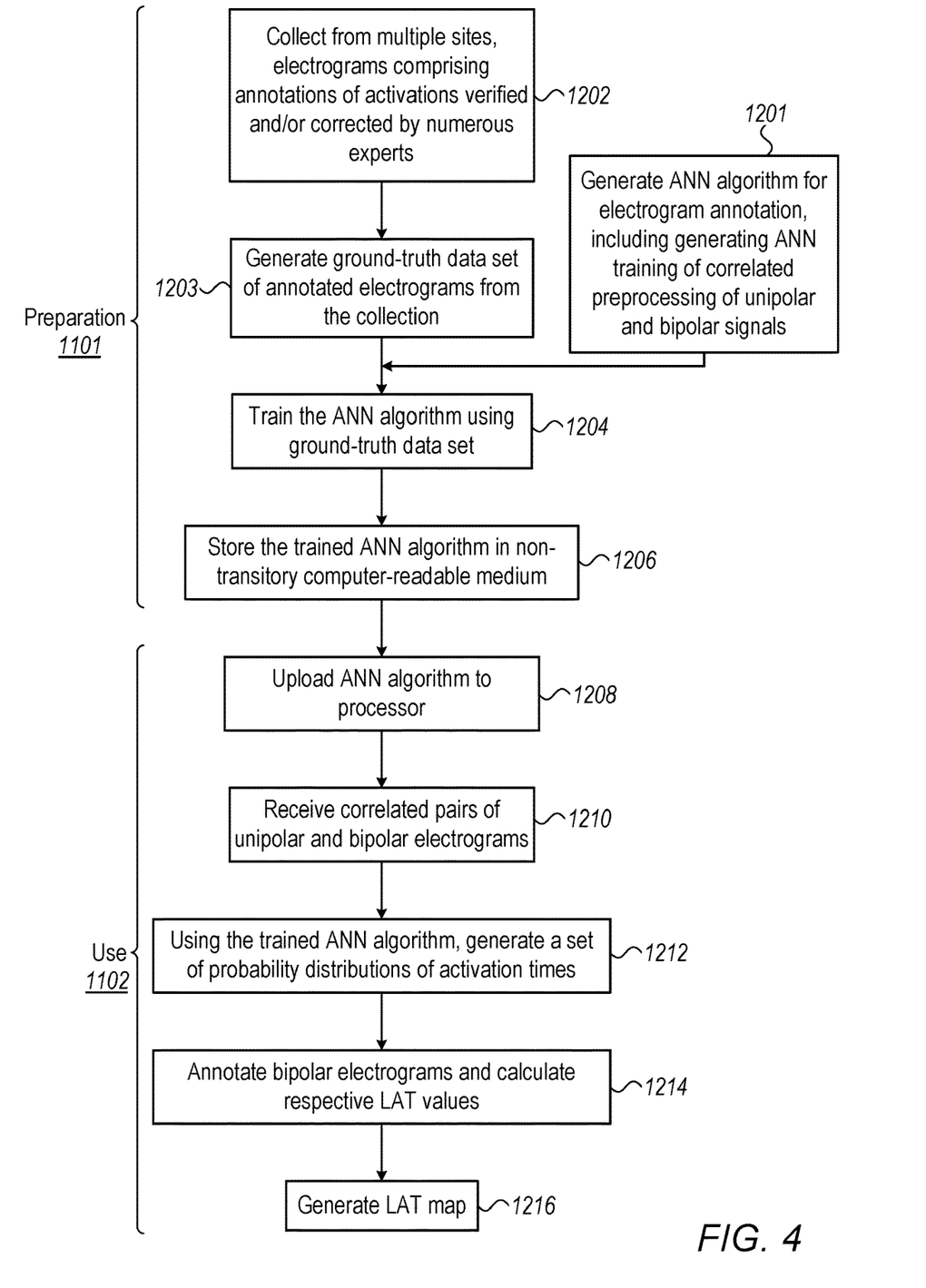
FIG. 4 is a flow chart that schematically illustrates a method and algorithm for detecting activation times in electrograms (EGM), annotating the activations, and generating an activation map, according to an exemplary embodiment of the present invention.

A Method of Detecting an Activation in EGM Using Ann-Trained Preprocessing Module FIG. 4 is a flow chart that schematically illustrates a method and algorithm for detecting activation in electrograms (EGM), annotating the activations, and generating an activation map, according to an embodiment of the present invention. The algorithm, according to the presented embodiment, is divided into two parts, algorithm and training data set preparation 1101 and algorithm use 1102.

Algorithm preparation carries out a process that begins at ANN modeling step 1201, with generating an ANN algorithm for detection of activation in an EGM, where the algorithm includes training of preprocessing of correlated unipolar and bipolar signals, such as the algorithm described in FIG. 3, that includes ANN trainable preprocessing module 300.

Independently, the training data base set preparation phase begins at a ground truth collection step 1202, that includes collecting from multiple sites (e.g., hospitals), electrograms comprising annotation of activations that were verified and/or corrected by numerous experts who are skilled at analyzing diagnostic cardiac electrograms.

At a ground truth data set generation step 1203, a person skilled in the art (e.g., a clinical application engineer, or an algorithm engineers) compiles from the collection of annotated electrograms, a ground truth data set to be used for training of the algorithm prepared in step 1201.

Next, using the ground truth data set of annotated electrograms, where the annotations are verified in step 1202 to be accurate, a processor trains the algorithm (e.g. the ANN and preprocessing parts), at an ML algorithm training step 1204.

The algorithm preparation ends with storing the trained model in a non-transitory computer-readable medium, such as a disc on key (memory stick), at a trained model storing step 1206. In alternative embodiments, the model is sent in advance, and its optimized parameters $\{\vec{x}, \vec{w}\}$ are sent separately after training.

Algorithm use 1102 carries out a process that begins at algorithm uploading step 1208, during which a user uploads to a processor either an entire ML model or its optimized parameters (e.g., $\{\vec{x}, \vec{w}\}$). Next, the processor, such as processor 28, receives bipolar and unipolar ECG signals, for example, from catheter 29, at EGM receiving step 1210.

Next, using the trained ANN model, the processor generates a set of probability distributions of activation times (typically, one distribution per one bi-polar EGM), at an EGM inference step 1212.

Figure 6A:
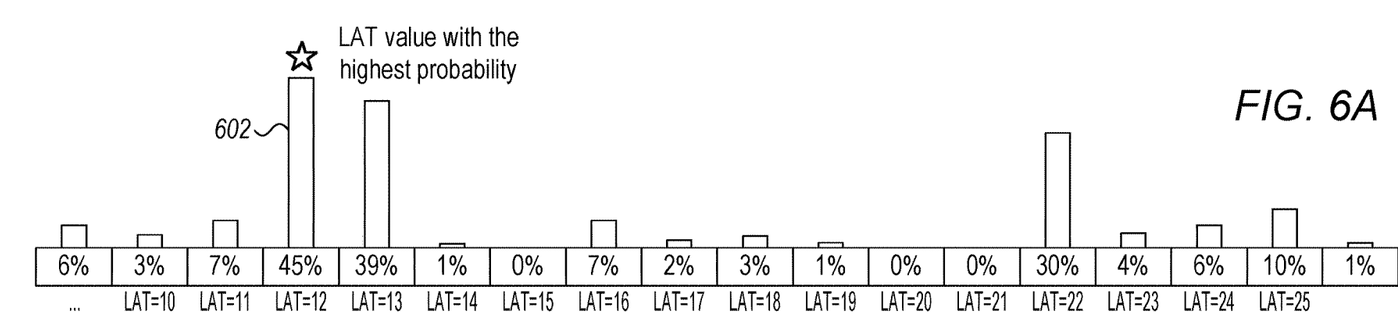
FIGS. 6A-6C are diagrams that illustrate selection of one or more local activation time (LAT) values from probability distributions of LAT values determined by the algorithm of FIG. 4, according to some exemplary embodiments of the present invention.

In some embodiments, a peak of a distribution may be selected in a subsequent step, i.e., beyond those included in the ANN model, so as to determine the annotation and the respective LAT value. Thus, a LAT extraction step 1214, the processor annotates the bipolar EGM, for example, according to criteria provided in FIG. 6, and extracts (e.g., calculates) corresponding LAT values. Note, any annotation that falls outside the WOI is ignored.

Finally, using a set of LAT values, processor 28 generates an LAT map of at least a portion of a cardiac chamber, at an LAT map generation step 1216.

The exemplary flow chart shown in FIG. 4 is chosen purely for the sake of conceptual clarity. The present embodiment may also comprise additional steps of the algorithm, such as receiving multiple bipolar and unipolar ECM signals, as well as receiving indications of the degree of physical contact of the electrodes with diagnosed tissue from a contact force sensor. This and other possible steps are omitted from the disclosure herein purposely in order to provide a more simplified flow chart.

Figure 5:
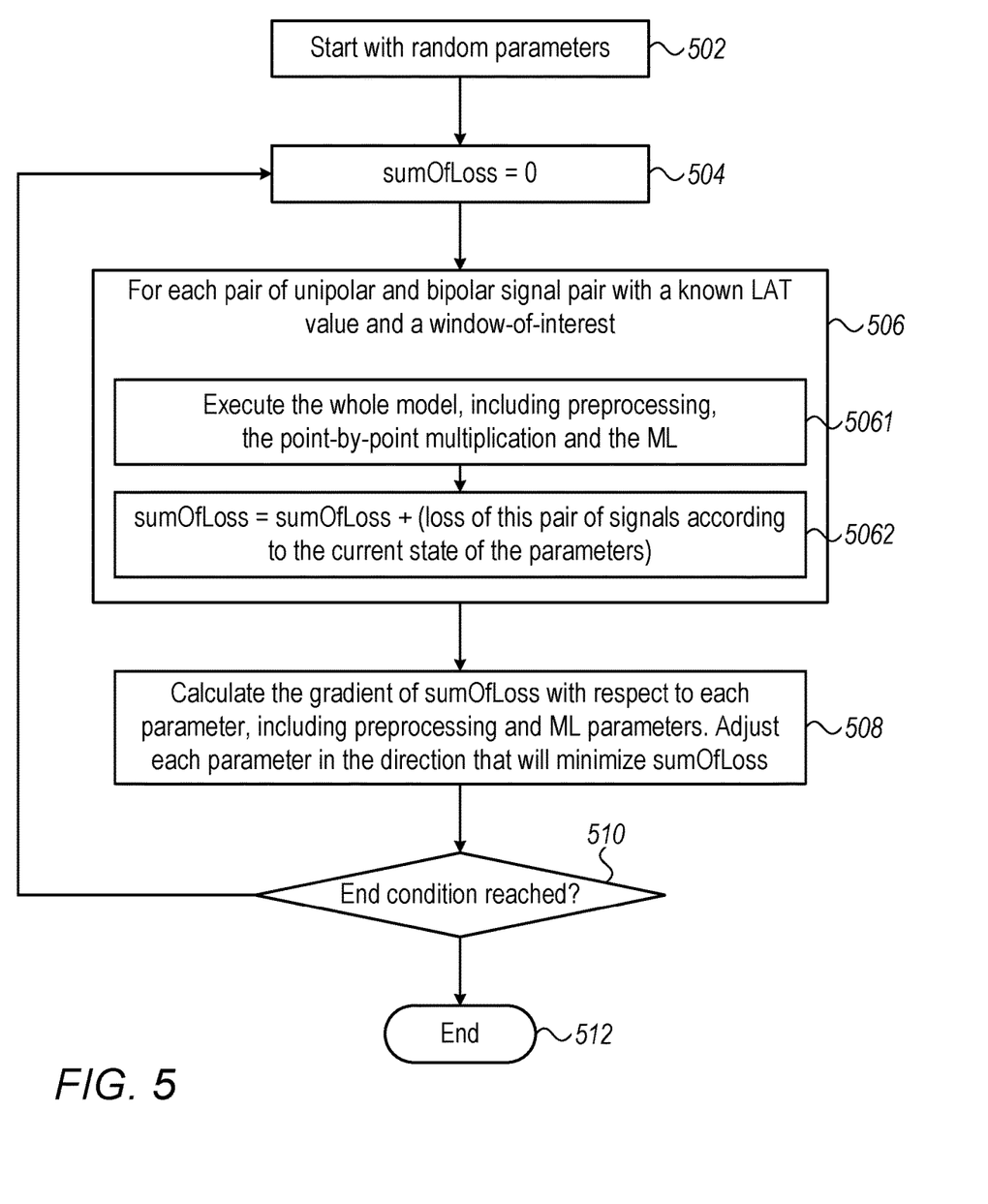
FIG. 5 is a flow chart that schematically illustrates a training method of the algorithm of FIG. 4, according to an exemplary embodiment of the present invention.

FIG. 5 is a flowchart that schematically illustrates a training method of the algorithm of FIG. 4, according to an embodiment of the present invention. The algorithm, according to the presented embodiment, carries out a process that begins at feeding the algorithm with random or pseudo-random parameters $\{\vec{x'}, \vec{w'}\}$, at a starting with random parameters step 502. Also, at a calculation initialization step 504, a sumOfTheLoss variable is set to zero.

Next, at a training step 506 parameters $\{\vec{x'}, \vec{w'}\}$ are used (5061) with the ground truth database of annotated EGM signals (e.g., verified LAT values). In step 5062, the processor calculate the loss of each signal with one of the loss functions described above, and calculates the sum of the losses, sumOfTheLoss.

In a gradient descent calculation step 508, the processor calculate the gradient of the sum of the losses with respect to each parameter. By looking into the gradients, adjust each parameter in the direction that will lower the loss.

In one embodiment, the training may be performed with the stochastic gradient descent method. During the training, $$\frac{\partial sumOfLoss}{\partial x_1}, \frac{\partial sumOfLoss}{\partial x_2}, \ldots, \frac{\partial sumOfLoss}{\partial x_m} \text{ and } \frac{\partial sumOfLoss}{\partial w_1},$$
$$\frac{\partial sumOfLoss}{\partial w_2}, \ldots, \frac{\partial sumOfLoss}{\partial w_n}$$

may be frequently calculated to adjust x and w values in the direction that will lower a sum of the loss. In this notation, x values relate to convolution kernels and w values relate to the ML algorithm. The training iterations optimize all values, x and w, as a whole to, when an end criterion is reached (510), yield the required optimized set of parameters $\{\vec{x}, \vec{w}\}$. At this point the process ends (512). If end condition has not reached, the process returns to step 504. The process may further terminated by another criterion, such as reaching a timeout.

Various methods, such as Stochastic Gradient Descent, Batch Gradient Descent, Mini-Batch Gradient Descent, Gradient Descent, Newton's method, also known as Newton-Raphson's method, can be used to converge the parameters by using the gradient values.

The end condition can be defined as the convergence of the sumOfTheLoss variable, the convergence of the parameters, the achievement of a sumOfTheLoss value lower than some threshold, a timeout, or a combination of them.

Analysis of Activation Values

As noted above, in some embodiments, the disclosed technique detects single activations (i.e., finds one LAT value per input electrogram waveform). In other embodiments, the technique is used to detect fractionated ECG signals, local abnormal ventricular activity (LAVA) indicative signals, late potentials, double potentials and split potentials. An embodiment designed to detect regular activations may choose the LAT value with the highest probability. An embodiment designed to detect double, split, fractionated, fragmented or any kind of multiple potentials may choose all LAT values with a probability above some threshold. An embodiment designed to detect late potentials can use a variable threshold, in a way that the later the LAT, the higher the threshold is. An embodiment to detect early potential can do the opposite.

Figure 6B:
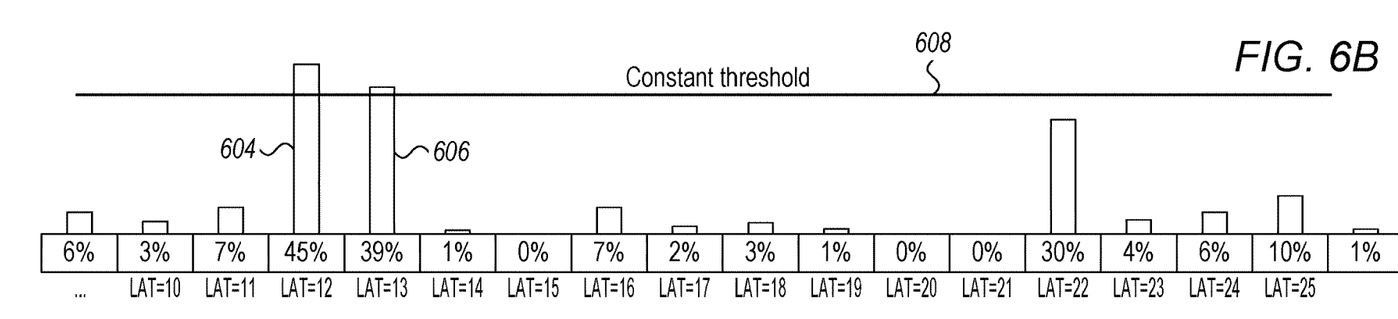
Figure 6C:
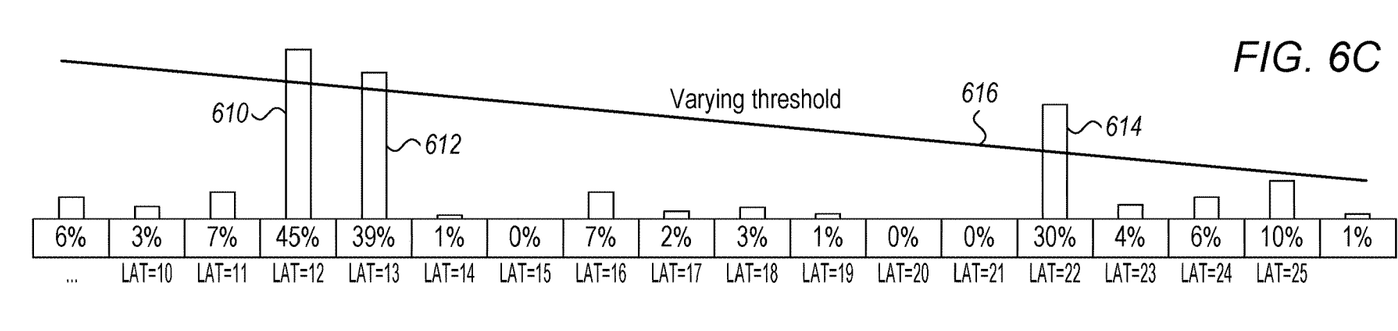

FIGS. 6A-C illustrate selection of one or more LAT values from probability distributions of local activation time (LAT) values determined by the algorithm of FIG. 4, according to some embodiments of the present invention.

FIG. 6A illustrates selecting the LAT value with the highest probability (602). This method finds, for example, regular activations.

FIG. 6B illustrates selecting all LAT values with a probability (604, 606) above a given threshold 608. This method can be used for finding, for example, double, split, fragmented, fractionated or any kind of multiple potentials. Double potentials play a critical role in the detection of lines of block or gaps in ablation lines. Fractionated potentials play a critical role in various arrhythmias, including atypical flutter and VT cases where the isthmus of the reentrant circuit or slow zones may exhibit varying fractionated potentials.

FIG. 6C illustrates a varying threshold 616, in a way that the threshold is lower for late LAT values 614 and higher for early values (610, 612). This method gives precedence to finding late arriving potentials. Finding late potentials plays a critical role in the ablation treatment of ischemic VT cases. Late potentials may be an indication of the slow conduction path of the reentrant circuit in scar-related VT cases and other cardiac pathologies.

For the clarity of FIGS. 6A-6C, in all the figures above, only LAT values between 10 mSec to 25 mSec are illustrated. In an actual system, the ANN should calculate probabilities for all LAT values in the window-of-interest. The width of the window of interest is typically similar to the cycle length of patient's arrhythmia. For example, if the patient is in a 200 beats per minute arrhythmia, the cycle length is 300 milliseconds. In this case, the physician may define the window of interest as, for example, −150 to +150 milliseconds around the reference annotation. In this specific example, our ML method will generate a probability for every LAT value between −150 and +150 milliseconds.

Although the embodiments described herein mainly address cardiac EP mapping systems, the methods and systems described herein can also be used in any medical application that needs to detect cardiac activations based on bipolar and unipolar intracardiac EGM signals, such as in intracardiac defibrillators (ICD) and artificial cardiac pacemakers.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A method, comprising:
    collecting a plurality of bipolar electrograms and respective unipolar electrograms of patients, the electrograms comprising annotations in which one or more human reviewers have identified and marked a window-of-interest and one or more activation times inside the window-of-interest;
    generating, from the electrograms, a ground truth data set for training at least one electrogram-preprocessing step of a Machine Learning (ML) algorithm, wherein the electrogram-preprocessing step comprises specifying coefficients of a set of convolutional kernels and performing one or more convolutions of the electrograms with the set of convolutional kernels and point-by-point multiplication between a bipolar electrogram filtered by one of the convolutional kernels and a respective unipolar electrogram filtered by another one of the convolutional kernels, wherein applying the ML algorithm comprises inputting a multiplication signal resulting from the point-by-point multiplication to the ML algorithm; and
    applying the ML algorithm to the electrograms, to at least train the at least one electrogram-preprocessing step, so as to detect an occurrence of an activation in a given bipolar electrogram within the window-of-interest.

2. The method according to step 1, wherein each bipolar electrogram is acquired from a pair of electrodes placed at a location in a heart of a patient, and wherein a respective unipolar electrogram is acquired from one electrode of the pair of electrodes.

3. The method according to claim 1, wherein collecting the bipolar electrograms and the respective unipolar electrograms comprises collecting multiple bipolar electrograms and respective unipolar electrograms from multiple electrode pairs of a multi-electrode catheter.

4. The method according to claim 1, and comprising presenting the given bipolar electrogram to a user, with an annotation thereon marking a time of detected activation.

5. The method according to claim 1, wherein applying the ML algorithm comprises applying an artificial neural network (ANN).

6. The method according to claim 1, and comprising:
    receiving for inference a bipolar electrogram and a respective unipolar electrogram of a patient, and a window-of-interest; and
    using the trained ML algorithm, detecting the occurrence of an activation in the bipolar electrogram and associating the activation with heart tissue location in contact with the electrode acquiring the respective unipolar electrogram.

7. A system, comprising:
    one or more displays, configured to present annotated electrograms; and
    one or more processors configured to:
        collect a plurality of bipolar electrograms and respective unipolar electrograms of patients, the electrograms comprising annotations in which one or more human reviewers have, using the one or more processors and the respective one or more displays, identified and marked a window-of-interest and one or more activation times inside the window-of-interest;
        generate, from the electrograms, in at least one of the one or more processors, a ground truth data set for training at least one electrogram-preprocessing step of a Machine Learning (ML) algorithm, wherein the electrogram-preprocessing step comprises specifying coefficients of a set of convolutional kernels and performing one or more convolutions of the electrograms with the set of convolutional kernels and point-by-point multiplication between a bipolar electrogram filtered by one of the convolutional kernels and a respective unipolar electrogram filtered by another one of the convolutional kernels, wherein applying the ML algorithm comprises inputting a multiplication signal resulting from the point-by-point multiplication to the ML algorithm; and apply the ML algorithm to the electrograms, to at least train the at least one electrogram-preprocessing step, so as to detect an occurrence of an activation in a given bipolar electrogram within the window-of-interest.

8. The system according to step 7, wherein each bipolar electrogram is acquired from a pair of electrodes placed at a location in a heart of a patient, and wherein a respective unipolar electrogram is acquired from one electrode of the pair of electrodes.

9. The system according to claim 7, wherein the one or more processors are configured to collect the bipolar electrograms and the respective unipolar electrograms comprises by collecting multiple bipolar electrograms and respective unipolar electrograms from multiple electrode pairs of a multi-electrode catheter.

10. The system according to claim 7, wherein the one or more processors are further configured to present the given bipolar electrogram to a user on the one or more displays, with an annotation thereon marking a time of detected activation.

11. The system according to claim 7, wherein the one or more processors are configured to apply the ML algorithm by applying an artificial neural network (ANN).

12. The system according to claim 7, wherein the one or more processors are further configured to:

receive for inference a bipolar electrogram and a respective unipolar electrogram of a patient, and a window-of-interest; and using the trained ML algorithm, detect the occurrence of an activation in the bipolar electrogram and associate the activation with heart tissue location in contact with the electrode acquiring the respective unipolar electrogram.

13. A method for identifying activations in cardiac electrograms using a Machine Learning (ML) model having at least one electrogram-preprocessing step, the method comprising:

training the at least one electrogram-preprocessing step of the ML model, wherein the electrogram-preprocessing step comprises specifying coefficients of a set of convolutional kernels and performing one or more convolutions of the electrograms with the set of convolutional kernels and point-by-point multiplication between a bipolar electrogram filtered by one of the convolutional kernels and a respective unipolar electrogram filtered by another one of the convolutional kernels, wherein applying the ML algorithm comprises inputting a multiplication signal resulting from the point-by-point multiplication to the ML algorithm; and identifying using the ML model, within a window-of-interest, an activation in a bipolar electrogram using a respective unipolar electrogram.

14. The method according to claim 13, wherein identifying the activation comprises generating, by the ML model, a respective probability for each of multiple possible activation values in the window of interest.

15. The method according to claim 13, wherein identifying the activation comprises selecting one of (i) an activation with the highest probability, (ii) one or more activations with a probability above a given threshold, and (iii) one or more activations with a probability above a variable threshold.

16. A computer software product, the product comprising a tangible non-transitory computer-readable medium in which program instructions are stored, which instructions, when read by a processor, cause the processor to implement the method of claim 1.

* * * * *